(12) United States Patent
Walker

(10) Patent No.: US 6,387,724 B1
(45) Date of Patent: *May 14, 2002

(54) METHOD OF FABRICATING SILICON-ON-INSULATOR SENSOR HAVING SILICON OXIDE SENSING SURFACE

(75) Inventor: Howard W. Walker, San Diego, CA (US)

(73) Assignee: Dynamics Research Corporation, Andover, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/258,716

(22) Filed: Feb. 26, 1999

(51) Int. Cl.$^7$ .............................................. H01L 21/00
(52) U.S. Cl. ............................................... 438/49
(58) Field of Search ................................ 257/252, 253, 257/414; 438/48, 49, 800; 204/416, 419, 426, 429, 433, 431, 413, 414

(56) References Cited

U.S. PATENT DOCUMENTS

| | | | |
|---|---|---|---|
| 4,133,725 A | 1/1979 | Afromowitz et al. | 204/195 |
| 4,505,799 A | 3/1985 | Baxter | 204/416 |
| 4,657,685 A | 4/1987 | Sibbald | 204/406 |
| 4,812,220 A | 3/1989 | Iida et al. | 204/403 |
| 4,816,118 A | 3/1989 | Oyama et al. | 204/418 |
| 4,889,612 A * | 12/1989 | Geist et al. | 204/416 |
| 4,903,099 A | 2/1990 | Sekiguchi et al. | 357/25 |
| 4,961,833 A | 10/1990 | Sakai et al. | 204/403 |
| 4,968,400 A | 11/1990 | Shimomura et al. | 204/403 |
| 4,975,175 A | 12/1990 | Karube et al. | 204/403 |
| 5,039,390 A | 8/1991 | Hampp et al. | 204/412 |
| 5,068,205 A | 11/1991 | Baxter et al. | 204/416 |
| 5,130,265 A | 7/1992 | Battilotti et al. | 437/40 |
| 5,192,417 A | 3/1993 | Oyama et al. | 204/418 |
| 5,309,085 A | 5/1994 | Sohn | 324/71.5 |
| 5,343,064 A * | 8/1994 | Spangler et al. | 257/350 |
| 5,350,701 A | 9/1994 | Jaffrezic-Renault et al. | 437/40 |
| 5,393,401 A | 2/1995 | Knoll | 204/418 |
| 5,407,854 A | 4/1995 | Baxter et al. | 437/54 |
| 5,414,284 A | 5/1995 | Baxter et al. | 257/253 |
| 5,511,428 A | 4/1996 | Goldberg et al. | 73/777 |
| 5,625,209 A | 4/1997 | Appleton et al. | 257/253 |
| 5,665,653 A | 9/1997 | Bare et al. | 438/49 |
| 5,786,608 A * | 7/1998 | Lescouzeres et al. | 257/253 |
| 5,944,970 A * | 8/1999 | Rosenblatt | 204/416 |
| 5,945,712 A * | 8/1999 | Kim | 257/347 |
| 6,022,754 A * | 2/2000 | Guillemet et al. | 438/49 |

* cited by examiner

Primary Examiner—Charles Bowers
Assistant Examiner—Craig Thompson
(74) Attorney, Agent, or Firm—Weingarten, Schurgin, Gagnebin & Lebovici LLP

(57) ABSTRACT

An ion-sensitive sensor has an active layer of silicon with source and drain diffusion regions of a field-effect transistor formed therein, patterned layers of silicon oxide and metal on one side of the active silicon layer, and a layer of insulative support material on the metal and silicon oxide layers. A continuous layer of silicon oxide on the other side of the active silicon layer has an exposed surface in the region of the field-effect transistor so that surface charge is formed in the exposed area of the continuous silicon oxide layer when placed in contact with an electrolyte solution. The surface charge induces a channel in the undiffused channel region between the source and drain regions, enabling the flow of current between source and drain contacts under proper bias conditions. The sensor is fabricated by a process that begins with the formation of a field-effect transistor on an active silicon layer of a silicon-on-insulator (SOI) wafer, and the subsequent formation of an insulative support layer over the active silicon layer. The substrate silicon of the SOI wafer is then removed, either by chemical or mechanical means, to expose the buried silicon oxide layer of the SOI wafer. The exposed oxide may form the ion-sensitive surface of the sensor, or additional modification treatment may be done to improve various characteristics of the sensing surface.

6 Claims, 1 Drawing Sheet

METHOD OF FABRICATING SILICON-ON-INSULATOR SENSOR HAVING SILICON OXIDE SENSING SURFACE

CROSS REFERENCE TO RELATED APPLICATIONS

None

STATEMENT REGARDING FEDERALLY SPONSORED RESEARCH OR DEVELOPMENT

Not Applicable

BACKGROUND OF THE INVENTION

The present invention is related to the field of ion-sensitive sensors, and in particular ion-sensitive sensors employing field-effect transistors (FETs) as sensing devices.

It is known to build pH sensors using ion-sensitive field-effect transistors (ISFETs). In such sensors, a FET is placed in contact with an electrolyte solution, which causes the conduction characteristics of the FET to change in a manner that depends on the pH or other ion concentration of the solution. The FET's conduction of current is detected by external circuitry which is calibrated in a manner such that the output of the circuitry is a digital or analog value representing the pH of the solution. This output can be used to drive a display or other processing circuitry as desired.

In general, prior ISFET sensors have been constructed such that the electrolyte solution contacts the FET in an area in which various circuit features of the FET are formed. These features include, for example, source and drain diffusions in the silicon substrate of the FET, and metal contacts that are used to provide electrical interconnection to the FET. It is not desirable for an electrolyte solution to contact these features, however, because improper operation or failure of the sensor can result. Thus prior ISFET sensors have generally employed some type of encapsulant to seal the FET from the electrolyte solution. Encapsulants are prone to leakage resulting from age-induced wear or other causes, and thus can contribute significantly to the failure of the ISFET sensors in which they are used.

It would be desirable to reduce or eliminate failure of ISFET sensors that arises from the use of encapsulants.

BRIEF SUMMARY OF THE INVENTION

In accordance with the present invention, an ion-sensitive sensor and a method of fabricating an ion-sensitive sensor are disclosed. The sensor employs a silicon-on-insulator (SOI) ISFET, and maintains the required sealing of source and drain contacts without requiring encapsulants. The sensor fabrication method is compatible with existing SOI processing, so that the sensor can be readily integrated with other CMOS circuitry to enhance the performance and packaging of systems in which the sensor is used.

The disclosed sensor has an active layer of silicon with source and drain diffusion regions of a field-effect transistor formed therein, patterned layers of silicon oxide and metal on one side of the active silicon layer, and a layer of insulative support material on the metal and oxide layers. A continuous layer of silicon oxide on the other side of the active silicon layer has an exposed surface in the region of the field-effect transistor to enable the formation of surface charge in the exposed area of the continuous silicon oxide layer when placed in contact with an electrolyte solution. The surface charge induces a conductive channel in the channel region of the FET between the source and drain regions, enabling the flow of current between source and drain contacts under proper bias conditions.

Because the ion-sensitive surface is on the oxide-protected backside of the FET, there is no requirement for an encapsulant to protect the topside circuit features. Further, because of its structure the sensor can be easily integrated with other CMOS circuitry, which enables the electrical and packaging aspects of a sensor system to be improved.

In the disclosed sensor fabricating method, a field-effect transistor is formed on an active silicon layer of a silicon-on-insulator (SOI) wafer, and then an insulative support layer is formed over the active silicon layer. An exemplary support layer is polyimide. The substrate silicon of the SOI wafer is then removed, for example by chemical or mechanical means, to expose the buried silicon oxide layer of the SOI wafer. The exposed oxide layer may itself form the ion-sensitive surface of the final sensor, or alternatively additional treatments may be used to modify the sensing surface.

This fabrication method results in sensors whose topside contacts and components need not be exposed to an ion solution for proper sensor operation, so that no subsequent encapsulation process is required. Additionally, the process is compatible with existing SOI wafer processing, so that sensors and other CMOS circuitry can be formed on the same SOI wafer, improving both electrical and packaging aspects of the system in which the resulting sensor is used.

Other aspects, features, and advantages of the present invention are disclosed in the detailed description which follows.

DETAILED DESCRIPTION OF THE INVENTION

Figure 1:
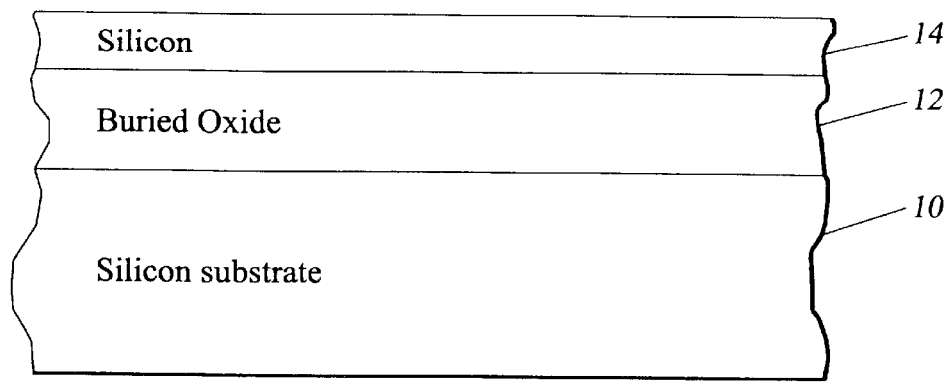
FIG. 1 is a schematic view of a section of a prior-art silicon-on-insulator (SOI) wafer which serves as starting material for the fabrication of an ion-sensitive field-effect transistor (FET) sensor according to the present invention.

FIG. 1 shows a prior-art silicon-on-insulator (SOI) wafer which serves as the beginning material for the fabrication of an ion-sensitive FET (ISFET) sensor. The wafer consists of a relatively thick silicon substrate 10, a substantially thinner layer of silicon oxide 12 commonly referred to as a "buried oxide" layer, and an outermost thin layer of silicon 14 commonly referred to as an "active" layer. Typical thicknesses for these layers in present technology are 500–700 microns for the silicon substrate 10, 380 nanometers (nm.) for the buried oxide layer 12, and 220 nm for the active silicon layer 14.

Figure 2:
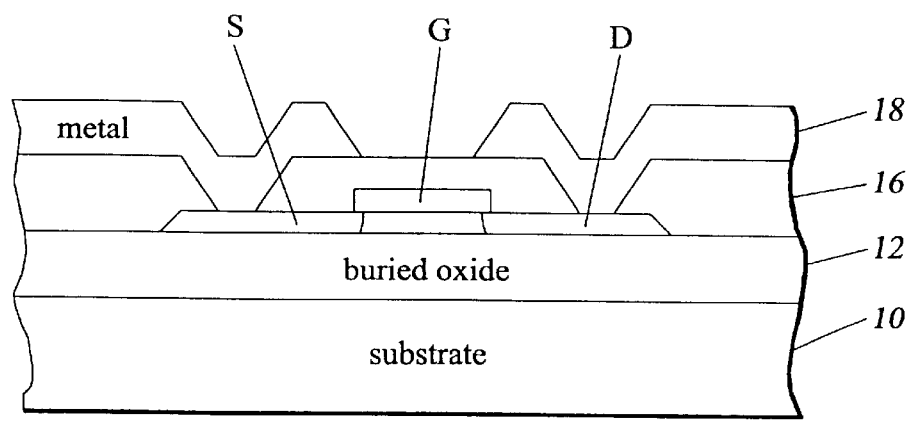
FIG. 2 is a schematic view of the SOI wafer of FIG. 1 after an SOI FET is formed thereon during the sensor fabrication process.

FIG. 2 shows the wafer of FIG. 1 after a number of conventional processing steps have been performed to create a field-effect transistor (FET). Source (S) and drain (D) diffusion regions have been formed in the active layer 12, and the area of the active layer 12 surrounding the FET has been removed. A small undiffused channel region remains underneath a polysilicon gate (G). A patterned layer of silicon oxide 16 covers most of the FET, including the gate G, except for openings above the source and drain regions. A patterned layer of metal 18 is formed above the oxide layer 16, and separate sections of the metal layer 18 contact the source and drain respectively to provide electrical interconnections between these regions and other electrical circuitry.

In a conventional FET, an opening in the insulating oxide layer 16 and a contact on metal layer 18 are formed for the gate electrode as well. Then during operation, a charge carrying channel is induced in the channel region under the influence of a voltage applied to the gate electrode under proper bias conditions. In the device of FIG. 2, however, the gate electrode is not actively involved in the operation of the FET. The gate serves primarily as a mask during the diffusions of the source and drain regions to create the undiffused channel region between them.

Figure 3:
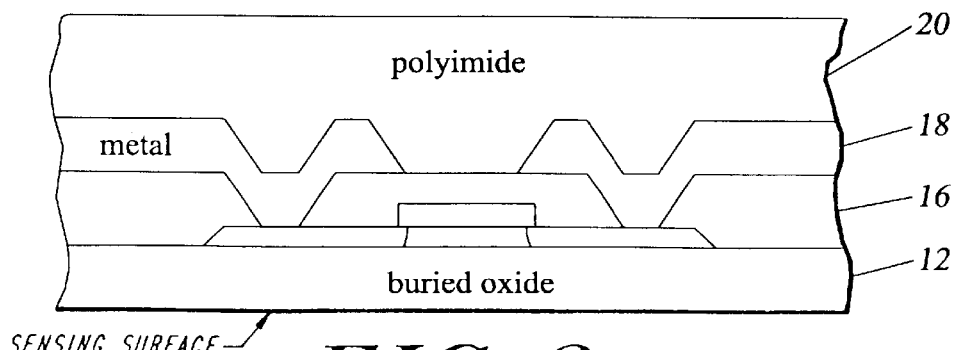
FIG. 3 is a schematic view of the SOI wafer and FET of FIG. 2 after the removal of the substrate silicon and bonding of an insulative support material on the top of the wafer.

FIG. 3 shows the wafer of FIG. 2 after additional processing that yields an ion-sensitive FET sensor. A polyimide layer 20 has been coated onto the wafer. The layer 20 serves several purposes in the sensor. It is an electrical insulator and a moisture barrier for the top side of the sensor. The polyimide layer 20 also provides mechanical support to help maintain the structural integrity of the sensor, because as described below the final sensor device is substantially thinner than the initial wafer due to removal of the silicon substrate 10 during subsequent processing.

FIG. 3 shows that all or substantially all of the silicon substrate 10 has been removed. This is accomplished by chemical etching and/or surface micro-machining. The removal of the silicon substrate 10 leaves one surface of the buried oxide layer 12 exposed, shown as a "sensing surface" in FIG. 3. During operation, the buried oxide layer 12 is placed in contact with an electrolyte solution. This results in the buildup of a surface charge in the oxide layer 12 at the sensing surface; the magnitude of the surface charge depends on the pH of the solution. When the source and drain regions are properly biased, the surface charge in the oxide layer 12 induces a conductive channel in the channel region of the FET, and source-drain current flows. The magnitude of the source-drain current is a function of the current-carrying capacity of the induced channel, which is dependent upon the magnitude of the surface charge in the oxide layer 12, which is in turn dependent upon the pH of the solution.

Various features of the above-described sensor and sensor fabrication method can be modified to achieve alternative embodiments. The thicknesses of the various layers on the starting SOI wafer may be varied. In this regard, both the thickness and the doping of the active silicon layer 14 affect the coupling between the surface charge on the oxide layer 12 and the FET, and therefore affect the sensitivity of the sensor. The sensing surface may be modified by the addition of layers such as silicon nitride or tantalum oxide, which can improve device characteristics such as sensitivity, linearity, hysteresis, etc.

The supporting layer 20 can be formed of alternative materials, such as Teflon, Kapton, or other packaging materials, and can be formed by different methods including deposition and bonding. Also, the supporting layer 20 may be a rigid or flexible circuit board substrate having conductors that interconnect the sensor with external circuitry.

In the illustrated embodiment the sensing surface is substantially planar, which is generally desirable. However, in alternative embodiments it may be desirable to limit the thinning of the substrate to just the channel region, in order to provide greater mechanical support for the device. The fabrication method can also be used to build other types of sensors. For example, a chemically modified gel can be placed in contact with the sensing surface of the oxide layer 12, and encapsulated with a permeable membrane. A gas or solution that permeates the membrane will interact with the gel such that its pH is changed. For example, the pH of a bicarbonate gel will be affected by the concentration of carbon dioxide gas with which it comes into contact. The change in pH of the solution can detected by the sensor to yield an indication of the concentration of the gas or solution.

It will be apparent to those skilled in the art that additional modifications to and variations of the above-described methods and apparatus are possible without departing from the inventive concepts disclosed herein. Accordingly, the invention should be viewed as limited solely by the scope and spirit of the appended claims.

What is claimed is:

1. A method of fabricating an ion-sensitive field-effect transistor sensor, comprising the steps of:

forming a field-effect transistor on an active silicon layer of a silicon-on-insulator (SOI) wafer, the active silicon layer being separated from a substrate silicon layer of the SOI wafer by a buried layer of silicon oxide;

forming an insulative support layer over the active silicon layer of the SOI wafer after the field-effect transistor has been formed thereon; and after the support layer has been formed, removing the substrate silicon layer of the SOI wafer to expose the buried silicon oxide layer.

2. A method according to claim 1, wherein the substrate-removing step comprises chemical etching of the substrate silicon.

3. A method according to claim 1, wherein the substrate-removing step comprises micro-machining of the substrate silicon.

4. A method according to claim 1, wherein the support-layer-forming step comprises bonding the support layer to the SOI wafer.

5. A method according to claim 1, wherein the support-layer-forming step comprises depositing support layer material on the SOI wafer.

6. A method according to claim 1, wherein the support layer is polyimide.

* * * * *